United States Patent
Doyle

(10) Patent No.: US 6,591,221 B1
(45) Date of Patent: Jul. 8, 2003

(54) METHOD AND DEVICE FOR ASSESSING CATTLE

(76) Inventor: John Conan Doyle, P.O. Box 1821, Tooowomba, Queensland, 4350 (AU)

( * ) Notice: Subject to any disclaimer, the term of this patent is extended or adjusted under 35 U.S.C. 154(b) by 0 days.

(21) Appl. No.: 09/720,141

(22) PCT Filed: Jun. 21, 1999

(86) PCT No.: PCT/AU99/00504

§ 371 (c)(1),
(2), (4) Date: Dec. 21, 2000

(87) PCT Pub. No.: WO99/67631

PCT Pub. Date: Dec. 29, 1999

(30) Foreign Application Priority Data

Jun. 22, 1998 (AU) ............................................. PP4227

(51) Int. Cl.$^7$ ............................................. G01B 11/02
(52) U.S. Cl. ..................... 702/159; 702/158; 702/173; 702/155; 702/160
(58) Field of Search ................................. 702/159, 158, 702/173, 155, 166, 19, 170, 171, 172

(56) References Cited

U.S. PATENT DOCUMENTS

| | | |
|---|---|---|
| 5,483,441 A | 1/1996 | Scofield |
| 5,576,949 A | 11/1996 | Scofield et al. |
| 5,673,647 A * | 10/1997 | Pratt ........................ 119/51.02 |

FOREIGN PATENT DOCUMENTS

| | | |
|---|---|---|
| CA | 2216309 | 3/1996 |

* cited by examiner

*Primary Examiner*—John Barlow
*Assistant Examiner*—Meagan Walling
(74) *Attorney, Agent, or Firm*—Millen, White, Zelano & Branigan, P.C.

(57) ABSTRACT

A method for assessing whether an animal has a total body fat or protein composition falling within a desired range, the method comprising the steps of: (a) obtaining a range of animal weight and a value selected from the group comprising pelvic height, frame score and animal size, such that animals having a weight and value within said range will have a total body fat or protein corresponding to the desired total body fat or protein, (b) measuring the pelvic height of said animal and if said value is frame score, further obtaining the age of the animal and calculating the frame score and where said value is animal size, further measuring the length of the animal and estimating the volume from the height and length measurements, (c) obtaining the weight of said animal and (d) comparing the value obtained in step (b) and the weight obtained in step (c) with the values obtained in step (a) and determining whether said obtained weight and value (c) and (d) fall within the range obtained in step (a) and if the obtained weight and value do fall within said range, then said animal has the desired body fat or protein composition.

14 Claims, No Drawings

METHOD AND DEVICE FOR ASSESSING CATTLE

FIELD OF THE INVENTION

The present invention relates to a method of assessing an animal's size through measurement of animal pelvic height with weight so as to enable extrapolation to estimate tissue composition of protein and fat. The method may be used to assess an animals' suitability for entry into a feeding program and/or slaughter. The present invention is also related to a device which may be used to assess animal size and relative body composition. The present invention is particularly directed towards assessing the suitability of beef cattle for entry into feeding programs and/or slaughter.

The present invention will be described with particular reference to beef cattle but it is understood that the method and device of the present invention may be used to characterize other suitable animals and no limitation is intended thereby.

BACKGROUND ART

In the meat industry, carcass quality is typically graded to a number of factors including weight, muscle shape (which corresponds to retail cut size) and fat distribution including subcutaneous, intra-muscular and kidney and pelvic fat. Animals younger than 20 months of age and/or less than 480 kg (i.e. equivalent empty body weight) are traditionally sold on subcutaneous fat deposition. Whereas, animals older than 20 months of age or greater than 550 kg (i.e. equivalent empty body weight) produce carcasses valued on quantity of intra-muscular fat. The primary fat content that infers meat quality is intramuscular rib-eye fat which is known as marbling.

An animals' genetics determines the potential quantity and distribution of fat deposition (i.e. subcutaneous, intra-muscular, kidney and pelvic fat). Expression of intra-muscular fat trait requires that the animal deposit a critical percentage of total body fat. Animals' slaughtered at an optimal percentage of total body fat content can potentially be more valuable than ones possessing a lower total body fat content and less marbling.

It is known that intramuscular fat deposition or marbling is enhanced as carcass fat increases to a certain level. Thus, an animal which is slaughtered at an optimal body fat content will be more valuable than an animal having lower total body fat and less marbling.

Animals are typically slaughtered at a target weight. Animal weight alone provides little or no information as to the factors referred to above. Thus by simply slaughtering an animal at a target weight, as is conducted presently in the industry, it is not possible to ascertain prior to slaughter the carcass quality. Carcass quality is only determined post slaughter.

A parameter that has been used to describe an animal's growth potential is frame size and/or frame score. This measurement describes an animal growth potential by pelvic height at age in months. It is typically used to describe frame size for breeding evaluation and experimental feeding programs. Frame score of an animal is described from its' sex, and pelvic height (cm ht) at a known age (i.e. month age). An animal maintains a frame score throughout life if allowed to consume adequate quantities of nutrients for potential growth. If age is approximated prior entry, pelvic height measurement can be obtained from entry and continued through the feeding program to assign an animal a frame score.

Physical measurements including pelvic measurement can be used to estimate animal characteristic such as skeletal and muscle development. Typical parameters used in such estimates are hip height and width, shoulder width and body length, Measurements of these parameters can be used to calculate shoulder muscle to bone ratio, rump muscle to bone ratio and musculoskeletal development per unit height and length. From these values, information about the relative amount of muscle to bone can be obtained. However, these values do not provide information about the extent of intramuscular fat deposition or marbling.

Animal feed performance (entry to finished weight) is measured through days on feed (DOF), average daily gain (ADG), and dry matter conversion (DMC). Animals' fed for similar days on feed possessing different growth patterns (i.e. referred to as large versus small frame animals) and body composition (i.e. percentage of total body protein and fat) upon entry to a feeding program can result in varied carcass traits. Animals are characterized as large frame because they possess greater growth potential (i.e. kilogram protein deposition) than small frame animals. The animals initial body composition upon entry to the feeding program and nutrient consumption influences feed performance followed by carcass quality.

Purchase requirement of animals includes sex, breed, weight and age. Animals are recognized by these parameters, however they are purchased on a weight basis and fed to a specified weight and/or number of days prior slaughter. Purchasing an animal by weight fails to describe frame size of animal. Describing and feeding animals based on frame size would have a large impact on achieving desired carcass quality. Example, animals enter the feedlot at a similar body weight, but possess different body composition (i.e. protein and fat). In order to achieve similar finished body tissue composition for uniform or specified carcass quality, animals must be fed to different finished weights. Animals that achieve similar percentages of total body fat and or protein produce uniform quality carcasses. Increasing carcass conformance to abattoir carcass specification or "grid" decreases monetary discounts and increases profitability. Decreasing required number of days on feed to obtain desired carcass quality end point increases profitability.

In view of the relationship between total body fat, carcass quality and feeding performance, the present inventor has recognised the desirability for a cattle farmer or feed lot manager to be able to estimate the total body fat of an animal prior to purchase or slaughter. As mentioned above, simple weight measurements which are currently used to asses cattle are quite inadequate for this purpose.

Many academic studies have been conducted on the body fat characteristics of animals and in particular cattle. Numerous methods have been used in these studies to measure animal total body protein and fat. Ultrasound units have been widely used for estimating subcutaneous fat at specific anatomical points and intra-muscular fat content at rib-eye area. Typically, an ultrasound transducer is placed on specific anatomical points to conduct signals. Protein, fat and bone content at these particular points are measured through differences of ultrasound wave signals. In order to describe subcutaneous and/or intra-muscular fat content of animal, a large number of individual measurements would be required at different anatomical points. Thus it would be quite time consuming and labor intensive to measure body fat by this method. Anatomical site preparation necessitates additional time required for the removal of loose hair, dirt and manure. Measuring animals with an ultrasound transducer requires prolonged restraint, stressing the animal.

Other information as to body fat of an animal may be obtained by surface fat measurements conducted using calipers. Fat content measurements of various organs and muscles may also be accomplished post slaughter.

Whilst the above methods for estimating fat may be suitable under research or limited commercial application, they are unsuitable for commercial operations such as saleyards or properties for monitoring large numbers of animals. Multiple ultrasound measurements of an animal are time consuming, labour intensive and require specialised personnel and equipment. Carcass quality measurements are obviously inappropriate for selecting animals for feeding programs and/or their suitability for slaughter.

Relationship between frame score, weight and total body fat or protein has been previously described in science literature. Example, observing animals of similar weights, large frame score has less total body fat or more protein whereas a small frame score animal has higher total body fat and less protein. Thus, having the knowledge of animal size and/or frame score of an animal with its weight permits estimates of total body fat and protein.

It is therefore an object of the present invention to provide a method of assessing an animal which employs the relationship between total body fat, frame score and weight of the animal. It is also an object of the present invention to provide a device which may be used to automatically measure a dimension of an animal such as pelvic height.

According to a first broad form of the present invention there is provided a method for assessing whether an animal has a total body fat or protein composition falling within a desired range, the method comprising the steps of:

(a) obtaining a range of animal weight and a value selected from the group comprising pelvic height, frame score and animal size, such that animals having a weight and value within said range will have a total body fat or protein corresponding to the desired total body fat or protein, (b) measuring the pelvic height of said animal and if said value is frame score, further obtaining the age of the animal and calculating the frame score and where said value is animal size, further measuring the length of the animal and estimating the volume from the height and length measurements, (c) obtaining the weight of said animal and (d) comparing the value obtained in step (b) and the weight obtained is step (c) with the values obtained in step (a) and determining whether said obtained weight and value (c) and (d) fall within the range obtained in step (a) and if the weight and value do fall within said range, then said animal has the desired body fat or protein composition.

In the method of the present invention, a desired range of total body fat or protein is selected and the corresponding range of animal size or frame score obtained. The body fat or protein composition will depend upon the purpose or market for which the animal is being selected. For example, an optimum body fat for an animal for desirable carcass quality is about 28 to 32 percent for some markets. Animals entering a feeding program possess lower percentage of total body fat than is desired prior slaughter.

The next step in the method is that weight ranges and animal sizes or frame scores which may be estimated to have the corresponding desired body fat or range thereof are obtained. This can be done by making use of known relationships between total body fat, animal size or frame score and weight and the known equations relating animal size or frame score to height. In estimating the desired weights and animal size or frame score, consideration should also be given to the animal's breed, sex and age.

The pelvic height of the animal is then measured. From these observations, a frame score may be assigned to an animal when age is known or estimated through dentition. This calculation is not necessary if the height has been obtained in step (a). If the value is size, the length of the animal is also measured. It will be appreciated that both animal length and age can be obtained to enable calculations of frame score and also the animal's size. Animal size estimates are generally represented in terms of animal volume.

The weight of the animal is then obtained. It will be appreciated that the height and weight of the animal may be obtained sequentially, in any order or at the same time. Where the animal's volume is calculated, the weight and volume range can be calculated as a weight/volume ratio or mass estimate.

It can be seen that selection or rejection of an animal based upon simply measuring the pelvic height and estimating the total body fat or protein can be accomplished relatively rapidly and efficiently versus detailed physical examination of the animal as description of the background art.

If the obtained value, whether it be height, animal size or frame score and weight fall within the ranges corresponding to desired total body fat, then the animal may be selected for entry into a feeding program or slaughter.

The method may also be used to assess an animal's growth rate and/or progress through a feeding program. If the animal does not have a desired total body fat, the feeding regime may be modified accordingly. Generally when assessing an animals' growth rate in a feed lot situation, measurements may be taken at intervals of between about 2 to about 4 months and typically at about every three months.

Further information concerning animal size can be estimated with greater accuracy by measuring other physical dimensions of an animal in addition to pelvic height and length. These additional measurements include shoulder height and shoulder width. Further animal parameters, such as surface area may also be able to calculated from the physical measurements.

It will also be appreciated that if desired, animal volume and frame score may both be calculated. This may provide still further information about the fat and protein composition of the animal.

The physical dimensions of the animal may be measured by any suitable means. However, it is desirable that the animal be measured as quickly and accurately as possible. Although the animal may be measured manually, for example, by being placed in front of a scale on a wall, this is manually intensive and also subject to error.

It is therefore a further object of the present invention to provide a device for automatically measuring physical dimensions of an animal and in particular a device for use in the method of the invention.

According to a second broad form of the invention, there is provided device for which includes measurement means for measuring the pelvic height of an animal, the device including a means for generating an ultrasound signal and directing said signal from a fixed position towards the pelvic region of the animal, means for receiving an ultrasound signal reflected from the surface of the animal and for measuring the time taken for the signal to be reflected and calculation means for calculating the pelvic height based upon the time taken for the signal to be reflected, the device further including means for inputting the weight and age of the animal and for calculating the frame score of the animal.

It will be appreciated that the above device may also be used as a convenient method to measure one or more physical dimensions of an animal. According to a third broad form of the invention there is provided an animal measuring device for measuring a physical dimension of an animal, the device including means for inputting information relating to the location of a reference point, a means for generating an ultrasound signal and directing said signal from a fixed position relative to the reference point towards a predetermined location on the surface of an animal, means for receiving an ultrasound signal reflected from the surface of the animal and for calculating the distance between the generating means and the predetermined location based upon the time taken for the signal to be reflected and means for calculating the physical dimension using the distance between the generating means and the animal's surface and the distance between the generating means and the reference point.

The device of the present invention enables a physical dimension of an animal to be measured by comparing the distances between an ultrasound generating means and a predetermined location on an animal and between the ultrasound generating means and a reference point. Typically the physical dimension to be measured is obtained by difference between the two distances.

Typically the device of the present invention is adapted to be fitted to known animal handling facilities such as holding chutes and/or animal crushes. Generally, a holding chute maintains or blocks an animals' entry into a crush. A crush is designed to hold an animal stationary during weighing and conducting dosing or veterinary procedures. In these known types of crushes an animal is typically restrained about the neck and shoulders. If desired, a pressure sensor may be placed on each side of the crush so as to enable the width across the animal's shoulders to be calculated.

The device is preferably used to measure the pelvic height of an animal, the top of the pelvis being the tallest part of the animal body. A reference point for use in measuring the pelvic height of the animal is typically located vertically below the pelvis on the ground surface on which the animal stands during measurement.

Preferably, when the pelvic height is to be measured, the animal is measured in the free standing position. It has been observed that when an animal is held by a crush, its normal stature may become distorted. Such distortion may lead to an error in height measurement.

Typically, the ultrasound generating means is located above the animal so as to direct the ultrasonic signal towards the dorsal section of the animals pelvic region. When the device is attached to a known animal holding chute, in which the animal is allowed to free stand (i.e. there is no distortion of its physical stature), the relative vertical location of the ultrasound generating means relative to the pelvis may vary with the length of the animal. However, as ultrasound signals are conical, the signal is received in a circular manner on the animal. Preferably, the signal is generated such that it has a diameter of between about 20 cm and about 60 cm and preferably between 35 and 50 cm and most preferably about 40 cm. This means that under most circumstances the precise location of the pelvis will receive at least some of the generated signal. Preferably, the means for calculating the distance between the ultrasound generating means and the animal includes means for being able to calculate the distance between the generating means and the highest point on the animal which reflects a signal. Thus, it is not necessary for the animal to be precisely positioned such that the pelvis is directly aligned with the ultrasound generating means.

The generating means may be mounted to a rail or the like to enable it to be moved such that its position relative to the pelvic region may be adjusted. This movement may be desirable if the device is to be used for measuring calves and cattle having a large size difference.

The device of the present invention may also be used to measure other physical dimensions either alternatively to or in addition to the animal's height.

Another physical dimension, which provides information as to an animal's size, is the length between the anterior shoulders and the caudal or tail region. Although the height of an animal may be distorted when held in a crush, there is believed to be a negligible effect on the animal's length. Thus, where the device is used to measure the animals length, it may be mounted to a conventional crush. Mounting to a crush has an advantage in that the animal is secured against the neck and point of shoulder. The reference point for measuring an animal's length is thus typically the point or the dorsal aspect of the humorous of the shoulders. The ultrasound generating means may be placed either directly behind the animal or at a slight angle above the animal such that the ultrasound signal is directed towards the tail head. Where the transducer is at an angle, it is generally necessary to be able to accurately measure the angle of transmission from the vertical or horizontal. Such angle measurement may suitable be accomplished by the use of a laser.

As mentioned above, the ultrasound signal is received over a generally circular area on the animal's back. Thus, animals having lengths within a certain range can be measured with the generating means being located in the same position. The range of lengths of animals which may be measured in this way may depend on the diameter of the ultrasound signal and the angle at which the signal is directed towards the animal. In order to measure animals outside a particular range, the ultrasound generating means may be mounted to a track or guide to enable it to be moved as desired.

The device of the present invention may also be used to measure the pelvic width of the animal. In this case, the device may include a pair of ultrasound generating means located on either side of the animal so as to measure the distance between the respective ultrasound generating means and the animal. Generally, the ultrasound generating means is mounted to opposing side walls of a holding chute and can measure the animal when it is free standing.

Typically the ultrasound signals are generated by a transducer. Such transducers are known. A typical transducer generates, amplifiers and transmits a signal. The signal is reflected from the animal and returns to the transducer. The signal is received, amplified and processed to provide information as to the distance of a location on the animal's surface to the transformer. A suitable transducer for use in the present invention directs a 1 millisecond tone burst, producing an output sound pressure level at 50 kHz of approximately 118 dB SPL at 1 meter. Typically the distances between the animal and transducer may be measured within 1 to 2 seconds.

The device of the present invention may include two or more transducers so as to enable more than one dimension to be measured. When the device includes two or more transducers, it is preferred that the signals from the respective transducers are do not interfere with each other. This may be achieved by programming the transducers to generate the ultrasound signals in an alternate manner.

Alternatively, the measurements can be made separately and typically sequentially. This can be conducted by either measuring the animal sequentially as it stands in a single location or by measuring one dimension with one transducer in a first position and then moving the animal to a second position for a second measurement to be taken.

In an especially preferred device in which both pelvic height and length are measured, the pelvic height will typically be measured using a first transducer mounted to a holding chute prior to entry into a crush. After measurement of the pelvic height, the animal is then allowed into the crush, the animal is secured about the neck and point of shoulder is against the gate. A second transducer, typically located horizontally behind the animal can then take the length measurement.

The device of the present invention may also include means for measuring the weight of the animal. However this is not necessary as the device may be adapted to be fitted to an existing weight scale device. Alternatively the weight of the animal may be determined at a different site and the information recorded or input as desired.

The device of the present invention may record and display data and results of calculations in a number of different manners. In one form of the invention, the device may simply include a display which provides a read out of the animals height. Alternatively, the device may further include computing means for calculating the frame score based upon the measurements made thereby. Still further, the device may include computing means for calculating the percent body fat and/or protein. In the latter two cases, it is preferred that provision be made for inserting relevant data relating to variables used in frame score calculation such as age, sex and breed.

Regardless of how the information is treated or displayed, it can be seen that it is a relatively straightforward matter to compare the display data with design characteristics which relate to body fat and/or protein. Thus an animal can be quickly assessed.

DETAILED DESCRIPTION OF THE PREFERRED EMBODIMENT

A preferred device of the present invention is fitted to a conventional cattle holding chute and crush combination in which an animals is contained in the holding chute, prior to entry into the crush. The holding chute has a front and a rear gate, allowing one animal to be held within this space to obtain a pelvic measurement. The crush has a front and rear gate and the animal is held by the front gate and the point of the shoulder of the animal is held firmly against the gate.

The device has a first ultrasound transducer mounted in the holding chute. The first transducer is located on a rail directly above the animal's pelvic region. The transducer may be of known type. The transducer is able to transmit a conical ultrasound signal which produces a signal having a 40 cm about the animal's pelvic region. This diameter of signal means that the point at which the animals' height is measured would normally receive at least some of the signal. The transducer may also be slidably mounted on a rail. Because of the diameter of the signal on the animal, it would normally not be necessary to move the transducer along the rail to accommodate animals of different lengths. However, should it be necessary to measure smaller animals, such as a calf, it is possible to slide the transducer along the rail so as to line the transducer up with the pelvic region.

The device includes a second transducer located near the rear gate of the crush. The second transducer is of the same type as the first transducer.

The first and second transducers are connected to a single computing means which is programmed to calculate the animals' height from the information received from the first transducer and the animal's length from the information obtained by the second transducer.

The first transducer generates a signal which is reflected from the animal's pelvic region to enable the pelvic height to be measured. The signal's diameter is wider than the point at which the height is measured and need not be in the center of the signal. The computing means can be programmed to enable the shortest distance which the ultrasound travels i.e. the highest point of the animal, to be calculated. The pelvic height of the animal is calculated by the difference between the distance between the transducer and the animal and a known distance between the transducer and the floor of the holding chute.

Initiation of the ultrasound signal can be done manually by an operator. Typically an operator will observe that the animal is in place in the chute and then activate the transducer. Alternatively such activation may be initiated automatically. For example the device may further include detection means such as an infra red device which can detect when an animal is present. After the animal's length has been measured in the holding chute, the front gate is opened and the animal is then allowed to pass through to the crush.

The second transducer is used in a similar manner to measure the length of the animal. The animal's length is calculated from the distance between the second transducer and the animal and the distance between the transducer and the animal's shoulders. The location of the animal's shoulders is known because the shoulders are held firmly against the front gate of the crush. The second transducer is activated when the animal is held by the crush. This can be done manually or automatically. The crush may include a pressure sensor in the front gate which can detect when the animal is firmly held and automatically activate the second transducer.

It can be seen that as the first and second transducers are operated in separately that signal interference can be minimized or avoided.

The device is controlled by a computing means which as described above calculates the pelvic height and length of the animal. Further data relating to the animal can also be input, either manually by an operator or automatically. For example, the computer means may be electronically connected to electronic scales for automatic measurement and input of the animal's weight.

Data which may be input manually includes the animals lot or identification number, the animals age (which may be determined by dentition), sex, breed, the market classification i.e. domestic and export, information relating to growth hormones, body condition score and any other general information or comments relating to the animal. Animal identification parameters may also be input automatically, for example by infra red analysis where the animal carries a bar coded tag. The device may also be programmed to record signals from animal's carrying internal identification transducers. Such internal means of identification is known.

Data such as age, sex, breed and the like can be stored in the computer such that there is no need for these values to be re-entered when the same animal is measured again.

After the measurements have been completed and calculations made, the data obtained may be represented on a computer screen. The data may also be saved for further manipulation at a later stage. A typical screen display would include the measurements for height (mm), length (mm), weight (kg) and weight/volume or mass estimate (kg/mm$^3$)

It can be seen that the method and device of the present invention allow animals to be rejected or selected according to meaningful measurements as opposed to the present method of simply measuring the weight of an animal.

The device of the present invention also enables automatic assessment of an animal. The device is simple and easy to use and can be installed in remote locations and operated by inexperienced personnel. Further, the use of ultrasound overcomes difficulties associated with known methods of measuring distances between. Such known methods include the use of laser and infrared signals to measure the distance between the laser or infrared source and an object. Typically, the distance is calculated from the time taken for a generated signal to be reflected from an object and received by a receiver. However laser and infrared are unsuitable for a number of reasons in the method and device of the present invention. First, the environments in which the device and method are to be used have large amounts of dirt, dust, animal hair and manure. The presence of such matter would scatter any laser or infrared signals making it difficult or impossible to measure a signal reflected from the animal. Also, because infra red and laser signals are quite narrow, in order to measure the distance between a precise location on an animal's body it would be necessary to accurately position the laser so as to direct the signal towards that location.

It should be appreciated that various other changes and modifications may be made to the embodiment described without departing from the spirit and scope of the invention as described.

What is claimed is:

1. A method for assessing whether an animal has a total body fat or protein composition falling within a desired range, the method comprising the steps of:
    (a) obtaining a range of animal weight and a value selected from the group comprising pelvic height, frame score and animal size, such that animals having a weight and value within said range will have a total body fat or protein corresponding to the desired total body fat or protein,
    (b) measuring the pelvic height of said animal and if said value is frame score, further obtaining the age of the animal and calculating the frame score and where said value is animal size, further measuring the length of the animal and estimating the volume from the height and length measurements,
    (c) obtaining the weight of said animal and
    (d) comparing the value obtained in step (b) and the weight obtained is step (c) with the values obtained in step (a) and determining whether said obtained weight and value (c) and (d) fall within the range obtained in step (a) and if the obtained weight and value do fall within said range, then said animal has the desired body fat or protein composition.

2. The method of claim 1, wherein in step (b) both the pelvic height and length of the animal are measured.

3. The method of claim 1, which further includes measuring the width of the animal.

4. The method of claim 1, wherein measurement of the animal is repeated over regular intervals to enable the growth of the animal to be assessed.

5. A method for assessing the total body fat or protein composition of an animal including the steps of:
    a) measuring the weight of the animal;
    b) determining an external value of the animal, said value selected from the group consisting of pelvic height, frame score and animal size wherein the pelvic height is measured, frame score is determined from the measure pelvic height and animal age, and animal size is determined from the measured pelvic height and animal length wherein the animal length is measured, and
    c) comparing the measured weight of the animal and the determined external value of the animal with a range of predetermined animal weights and value corresponding to total body fat or protein compositions to obtain an assessed total body fat or protein composition of the animal.

6. A method according to claim 5 wherein the pelvic height of the animal is measured using an ultrasound generating means.

7. A method according to claim 5 wherein the animal length is measured using an ultrasound generating means.

8. A method according to claim 5 wherein animal size is further determined from an additional measurement of pelvic width.

9. A method according to claim 8 wherein pelvic width is measured using an ultrasound generating means.

10. A method for assessing the total body fat or protein composition of an animal including the steps of:
    a) measuring the weight of the animal;
    b) determining only external values of the animal, said values consisting essentially of pelvic height, frame score and animal size wherein the pelvic height is measured, frame score is determined from the measure pelvic height and animal age, and animal size is determined from the measured pelvic height and animal length wherein the animal length is measured, and
    c) comparing the measured weight of the animal and the determined external values of the animal with a range of predetermined animal weights and value corresponding to total body fat or protein compositions to obtain an assessed total body fat or protein composition of the animal.

11. A method according to claim 10 wherein the pelvic height of the animal is measured using an ultrasound generating means.

12. A method according to claim 10 wherein the animal length is measured using an ultrasound generating means.

13. A method according to claim 10 wherein animal size is further determined from an additional measurement of pelvic width.

14. A method according to claim 13 wherein pelvic width is measured using an ultrasound generating means.

* * * * *

UNITED STATES PATENT AND TRADEMARK OFFICE
CERTIFICATE OF CORRECTION

PATENT NO. : 6,591,221 B1
DATED : July 8, 2003
INVENTOR(S) : John C. Doyle et al.

It is certified that error appears in the above-identified patent and that said Letters Patent is hereby corrected as shown below:

Title page,
Item [76], Inventors, "Tooowomba" should read -- Toowomba --.

Column 9,
Line 50, "obtained is step" should read -- obtained in step --.

Column 10,
Lines 11-12, "measure pelvic" should read -- measured pelvic --.
Line 38, "from the measure" should read -- from the measured --.

Signed and Sealed this

Twenty-second Day of March, 2005

JON W. DUDAS
*Director of the United States Patent and Trademark Office*